US012788907B2

(12) United States Patent
Xu et al.

(10) Patent No.: US 12,788,907 B2
(45) Date of Patent: Nov. 10, 2026

(54) POWDER INHALATION DEVICE AND MEDICAMENT BOX

(71) Applicant: SUZHOU XINMAIDE MEDICAL DEVICE TECHNOLOGY CO., LTD, Suzhou (CN)

(72) Inventors: Saihua Xu, Suzhou (CN); Xiaoyuan Sun, Suzhou (CN); Guangtao Zhao, Suzhou (CN)

(73) Assignee: Suzhou Xinmaide Medical Device Technology Co. Ltd., Suzhou (CN)

( * ) Notice: Subject to any disclaimer, the term of this patent is extended or adjusted under 35 U.S.C. 154(b) by 0 days.

(21) Appl. No.: 19/436,362

(22) Filed: Dec. 30, 2025

(65) Prior Publication Data

US 2026/0124408 A1 May 7, 2026

Related U.S. Application Data

(63) Continuation of application No. PCT/CN2023/133189, filed on Nov. 22, 2023.

(30) Foreign Application Priority Data

Jul. 7, 2023 (CN) ......................... 202310828770.4
Jul. 7, 2023 (CN) ......................... 202321775073.0
(Continued)

(51) Int. Cl.
*A61M 15/00* (2006.01)

(52) U.S. Cl.
CPC ...... *A61M 15/0046* (2014.02); *A61M 15/002* (2014.02); *A61M 15/0026* (2014.02);
(Continued)

(58) Field of Classification Search
CPC ............ A61M 15/0046; A61M 15/002; A61M 15/0026; A61M 15/0035;
(Continued)

(56) References Cited

U.S. PATENT DOCUMENTS 5,392,768 A * 2/1995 Johansson ............. G01F 13/006
128/200.14
6,488,027 B1 * 12/2002 Moulin ............. A61M 15/0028
128/203.15
(Continued)

FOREIGN PATENT DOCUMENTS

CN 106999683 A 8/2017
CN 107041986 A * 8/2017
(Continued)

*Primary Examiner* — Brandy S Lee
*Assistant Examiner* — Tina Zhang
(74) *Attorney, Agent, or Firm* — FisherBroyles, LLP

(57) ABSTRACT

Disclosed is a powder inhalation device and a medicament box, the powder inhalation device including a carrier plate, a mouthpiece, an air intake slot and an air intake slot, where the carrier plate is formed with a through hole, and an annular groove is provided at an outer periphery of the through hole; the mouthpiece is disposed above the carrier plate; the capsule chamber is disposed under the carrier plate, and the capsule chamber also communicates with an outside atmosphere; air intake slots are spaced around the outer periphery of the through hole, each of the air intake slots including a horizontal slot section and an oblique slot section; and the horizontal slot section is located on an upper surface of the carrier plate, the oblique slot section is located on a sidewall of the annular groove, and the horizontal slot section is connected to the oblique slot section.

19 Claims, 14 Drawing Sheets

A-A

(30) Foreign Application Priority Data

Jul. 14, 2023 (CN) ........................ 202321848737.X
Jul. 21, 2023 (CN) ........................ 202321928949.9

(52) U.S. Cl.
CPC .... *A61M 15/0035* (2014.02); *A61M 15/0041* (2014.02); *A61M 2202/0007* (2013.01); *A61M 2202/064* (2013.01); *A61M 2205/0233* (2013.01); *A61M 2205/3331* (2013.01); *A61M 2205/583* (2013.01); *A61M 2205/7545* (2013.01); *A61M 2206/20* (2013.01); *A61M 2210/0625* (2013.01)

(58) Field of Classification Search
CPC .... A61M 2202/0007; A61M 2202/064; A61M 2205/0233; A61M 2205/3331; A61M 2205/583; A61M 2205/7545; A61M 2206/20; A61M 2210/0625; A61M 15/0021; A61M 15/003–0041; A61M 15/0086
See application file for complete search history.

(56) References Cited

U.S. PATENT DOCUMENTS

| | | | | |
|---|---|---|---|---|
| 8,251,059 | B2 * | 8/2012 | Nishibayashi | A61M 15/0005 128/203.19 |
| 2005/0103336 | A1 | 5/2005 | Nishibayashi et al. | |
| 2008/0105256 | A1 * | 5/2008 | Lulla | A61M 15/0028 128/203.21 |
| 2013/0061851 | A1 * | 3/2013 | Jones | A61M 15/0028 128/203.15 |
| 2013/0255679 | A1 | 10/2013 | Andrade et al. | |
| 2017/0014583 | A1 * | 1/2017 | Koerner | A61M 15/0021 |
| 2017/0215485 | A1 * | 8/2017 | Zitzke | A24F 40/53 |
| 2018/0361085 | A1 * | 12/2018 | Malhotra | A61M 15/0036 |
| 2019/0344025 | A1 | 11/2019 | Esteve | |
| 2024/0207540 | A1 * | 6/2024 | Dayioglu | A61M 15/0008 |

FOREIGN PATENT DOCUMENTS

| | | | | | |
|---|---|---|---|---|---|
| CN | 107149715 | A | | 9/2017 | |
| CN | 107469206 | A | * | 12/2017 | A61M 15/0071 |
| CN | 207429484 | U | | 6/2018 | |
| CN | 207591054 | U | | 7/2018 | |
| CN | 207591055 | U | | 7/2018 | |
| CN | 207591056 | U | | 7/2018 | |
| CN | 207591057 | U | | 7/2018 | |
| CN | 207591058 | U | | 7/2018 | |
| CN | 207591059 | U | | 7/2018 | |
| CN | 207605206 | U | | 7/2018 | |
| CN | 207640761 | U | | 7/2018 | |
| CN | 111135403 | A | * | 5/2020 | |
| CN | 217138881 | A | | 8/2022 | |
| CN | 217138881 | U | * | 8/2022 | |
| CN | 115105696 | A | * | 9/2022 | A61M 15/0021 |
| SG | 122174 | A1 | | 6/2006 | |
| WO | 2022206340 | A1 | | 10/2022 | |

* cited by examiner

POWDER INHALATION DEVICE AND MEDICAMENT BOX

CROSS REFERENCE TO RELATED APPLICATIONS

The present application is a continuation of the international application PCT/CN2023/133189, filed on Nov. 22, 2023 and entitled "powder inhalation device and a medicament box", and the international application claims the right of priority of the Chinese Patent Application No. 202321775073.9 filed on Jul. 7, 2023 and entitled "powder inhalation device with closing mechanism and medicament box", Chinese Patent Application No. 202310828770.4 filed on Jul. 7, 2023 and entitled "powder inhalation device with anti-misoperation mechanism and medicament box", Chinese Patent Application No. 202321848737.X filed on Jul. 14, 2023 and entitled "powder inhalation device with auxiliary air inlets and medicament box", and Chinese Patent Application No. 202321928949.9 filed on Jul. 21, 2023 and entitled "powder drug inhaler with a detachable base", which are incorporated herein by reference in their entirety.

TECHNICAL FIELD

The present invention relates to the technical field of powder inhalers, and in particular to a powder inhalation device and a medicament box.

BACKGROUND

At present, pulmonary inhalation administration is the best treatment for pulmonary diseases such as asthma and chronic obstructive pneumonia. In recent years, it has been extended to the treatment of systemic diseases such as diabetes, and has enormous market potential. Pulmonary administration requires the use of a specific delivery device to complete the dispersion, nebulization and pulmonary delivery of drug, and an inhaler plays a key role in a pulmonary administration system.

The existing powder inhalers can be roughly divided into three categories:

Class I: Provided is a depot-type powder inhaler having a reservoir in which a dose of powder can be stored, where the powder inhaler also has a dosing component that can separate a dose of powder from the reservoir each time it is actuated, and the separated powder is then inhaled into the patient's body through a drain line. Disadvantages of such powder inhalant: firstly, the amount of powder per delivery is inconsistent; secondly, this type of powder inhaler is poorly sealed, so the powder is susceptible to moisture in a humid environment, affecting an expected effect; finally, during the process of powder separation in the reservoir, part of the powder will remain inside the powder inhaler, which will contaminate the powder inhaler and cause certain harm to a user.

Class II: Provided is a multi-dose powder inhaler in which powder is stored separately in advance in blisters on a blister strip, where the blisters are evenly distributed on the blister strip, and the blister strip is mounted on a rotating disk inside the powder inhaler; Each actuation of the powder inhaler opens one blister, and the powder is inhaled into the patient's body through a discharge tube. Such powder inhaler better guarantees the sealing of the powder; and its disadvantages are: firstly, it has poor reproducibility, and there variation in the dose delivered to the patient between successive uses of the same powder inhaler; secondly, there will be powder residues in the powder inhaler, which will contaminate the powder inhaler and cause certain harm to a user; finally, there will be powder residues in the blister, causing the performance of the powder to not achieve an expected effect.

Class III: Provided is a single-dose powder inhaler in which powder is stored independently in a single capsule in advance, where capsules are distributed on a capsule plate, and when in use, a patient first takes out a capsule from the capsule plate, then puts the removed capsule into a capsule chamber of the powder inhaler, and presses a button to enable the capsule to be punctured, so that the powder is inhaled into the patient's body through a discharge tube.

SUMMARY

The present invention provides a powder inhalation device, including:

a carrier plate, a through hole being formed in the carrier plate, and an annular groove being provided at an outer periphery of the through hole;

a mouthpiece, the mouthpiece being disposed above the carrier plate and communicating with the through hole; and a capsule chamber, the capsule chamber being disposed under the carrier plate and communicating with the through hole, the capsule chamber also communicating with an outside atmosphere for inhalation of a first airflow;

where the powder inhalation device further includes:

at least one air intake slot, the air intake slot being provided at the outer periphery of the through hole, and the air intake slot including a horizontal slot section and an oblique slot section;

where the horizontal slot section is located on an upper surface of the carrier plate, the oblique slot section is located on a sidewall of the annular groove, and the horizontal slot section is connected to the oblique slot section, so that a second airflow drawn from the air intake slot creates a turbulent flow at the annular groove.

In some embodiments, the sum of surface areas of the horizontal slot section and the oblique slot section is positively related to an air intake amount of the air intake slot; and an included angle between the horizontal slot section and the oblique slot section is negatively related to the air intake amount of the air intake slot.

In some embodiments, the sum of the surface areas of the horizontal slot section and the oblique slot section is 2.65-2.95 $mm^2$; and the included angle between the horizontal slot section and the oblique slot section is 110-120°.

In some embodiments, three air intake slots are provided, the air intake slots being distributed circumferentially uniformly at the outer periphery of the through hole.

In some embodiments, the air intake slot further includes a draft slot section; and the draft slot section is located on the upper surface of the carrier plate and is disposed at an end of the horizontal slot section away from the oblique slot section, and the draft slot section and the horizontal slot section and the oblique slot section are integrally formed.

In some embodiments, a sieve mesh is arranged between the mouthpiece and the carrier plate, the sieve mesh is located at the through hole, and the sieve mesh is configured to intercept large particles of powder that have not been broken up.

In some embodiments, a sieve holder is provided inside the mouthpiece;

the sieve holder is partially provided in the annular groove and forms an airflow channel with the air intake slot, and at least two first snap-fits are provided at an outer periphery of the sieve holder;

the carrier plate is provided with at least two first snap-fit grooves, the first snap-fit grooves corresponding to and matching the first snap-fits; and the sieve holder is snap-fitted and fixed to the carrier plate by the first snap-fits and the first snap-fit grooves, and a sieve mesh is provided in the sieve holder.

In some embodiments, a lower shell is further included, the top of which is open;

where the carrier plate is hinged with the lower shell and is snap-fitted to the top of the lower shell; and the capsule chamber is housed inside the lower shell.

In some embodiments, the lower shell includes an outer shell and an inner shell;

the outer shell is provided with an opening on each side of the capsule chamber, and two sides of the opening are symmetrically provided with notch structures; and the inner shell has upwardly extending side panels on both sides, the side panels are at least partially engaged with the notch structures to secure the inner shell within the outer shell, while part of the side panel is of a transparent structure and a viewing window is formed at the corresponding opening.

In some embodiments, the notch structure is provided with a limit block, and the limit block is configured to limit the position of the inner shell; and an auxiliary column is provided at an inner bottom of the inner shell, and the auxiliary column is configured to correct and position the capsule chamber.

In some embodiments, steps are provided on two sides of the top of the lower shell, and each of the steps is provided with a second snap-fit groove at a hinge point away from the lower shell;

flanges are provided on both sides of the carrier plate, and each of the flanges is provided with a second snap-fit at a hinge point away from the carrier plate; and the flange is provided on the step and is snap-fitted and fixed to the second snap-fit groove by the second snap-fit, so that the carrier plate is detachably connected to the lower shell.

In some embodiments, an air intake gap is formed between the carrier plate and the lower shell, and the air intake gap is in communication with the bottom of the capsule chamber, so that the first airflow enters the capsule chamber through the air intake gap.

In some embodiments, an operating mechanism with a lancet is also included;

where the operating mechanism is movably arranged on a sidewall of the lower shell, and the operating mechanism is configured as a dual function actuator;

in a first actuation, the operating mechanism is capable of driving the upper shell to open; and in a second actuation, the operating mechanism is capable of driving the lancet to pierce a target capsule in the capsule chamber.

In some embodiments, the operating mechanism has guide plates parallel to the lancet, and a backstop is provided at an end of each of the guide plates close to the capsule chamber;

a guiding plate is provided on a side of the capsule chamber facing the operating mechanism, and the guiding plate is formed with a guiding hole; and the guide plate is slidably inserted into the guiding hole, and an anti-release function is realized by the backstop.

In some embodiments, an upper shell is also included, the bottom of which is open;

where one side of the upper shell is hinged with the carrier plate, and the other side of the upper shell is provided with a closure;

an interference surface is provided on a side of the carrier plate close to the operating mechanism;

a boat-shaped recess is provided at the top of the operating mechanism;

when the upper shell is in a closed state, the closure is located just inside the boat-shaped recess and is held against the interference surface; and only if an acting force exerted by the boat-shaped recess on the closure is larger than an interference force between the closure and the interference surface, the closure is capable of being disengaged from the interference surface and automatically opening the upper shell.

In some embodiments, the closure includes a guide portion and an interference portion arranged in sequence from bottom to top;

where the guide portion is in sliding fit with the boat-shaped recess to provide an acting force for driving the interference portion away from the interference surface.

In some embodiments, an included angle between the interference surface and a horizontal plane is 50-70°.

In some embodiments, the carrier plate, the mouthpiece, the lower shell and the upper shell are connected by a hinge pin.

In some embodiments, an inner wall of the mouthpiece and an inner wall of the capsule chamber are provided with a first conductive layer;

an outer surface of the lower shell is provided with a second conductive layer; and the first conductive layer is electrically connected to the second conductive layer so that static electricity generated by the use of the powder inhalation device is conducted out through a human body.

In some embodiments, the inner shell and the capsule chamber are made of a transparent plastic material, and the outer shell is made of a non-transparent plastic material; and the second conductive layer and the inner shell form a cross structure.

In some embodiments, an inner part of the mouthpiece and an inner wall of the capsule chamber are provided with a first conductive layer;

the lancet is a conductive lancet;

a third conductive layer is provided on a surface of the operating mechanism, or the inside of the operating mechanism is provided with a third conductive layer extending to the outside; and the first conductive layer is electrically connected to the third conductive layer by the lancet so that static electricity generated by the use of the powder inhalation device is conducted out through a human body.

In some embodiments, an inner wall of the mouthpiece and an inner wall of the capsule chamber are provided with a first conductive layer;

the lancet is a non-conductive lancet, and the lancet extends to a surface of the operating mechanism and has a metal filler disposed therein; and the first conductive layer contacts a human body through the metal filler so that static electricity generated by the use of the powder inhalation device is conducted out through the human body.

In some embodiments, a pressing rib is provided at an inner top of the upper shell, and a lower end of the pressing rib is held against a top end of the mouthpiece; and when the upper shell is flipped and closed, the unclosed mouthpiece is capable of being flipped in the same direction under the action of the pressing rib until it is completely closed on the carrier plate.

In some embodiments, an end of the lancet close to the capsule chamber is of a multifaceted structure, the multifaceted structure including a main oblique piercing surface and lateral piercing surfaces on two sides of the main oblique piercing surface.

In some embodiments, a fixing portion is provided at the bottom of the sieve holder; and the sieve mesh is provided at the fixing portion, and the two are fixedly connected by means of hot melting.

In some embodiments, a spring is arranged between the capsule chamber and the operating mechanism;

a rib is provided on a side of the capsule chamber facing the operating mechanism;

a cross-shaped protrusion is provided on a side of the operating mechanism facing the capsule chamber, and four sides of the cross-shaped protrusion extend outward and form a reinforcing rib structure in the operating mechanism; and two ends of the spring are fitted over the rib and the cross-shaped protrusion, respectively. Also provided is a medicament box, including a powder inhalation device of any one of the above.

Compared with the prior art, the beneficial effects of the present invention include at least:

1. By optimizing an auxiliary air intake structure, a turbulent flow near an annular groove is enhanced, allowing powder to be sufficiently dispersed, thus improving the effect of inhalation administration.
2. The auxiliary air intake structure does not affect a mounting structure at a through hole, which avoids an operating obstacle caused by weakening of a connecting force between a capsule chamber and a carrier plate, and improves the reliability of the device.
3. Inhaled powder can be screened for particle size, and a sieve mesh is easy to clean or replace.
4. A split lower shell is simple to manufacture and has a low maintenance cost, which also significantly reduces patient usage costs.
5. It has an anti-misoperation function, and a patient needs to give a certain force to an operating mechanism before it is unlocked for use, which improves the reliability of the device.
6. It has a good antistatic function to prevent the powder from being deposited in a mouthpiece and the capsule chamber due to electrostatic charge adsorption and being unable to be released, and affecting a powder utilization rate and a therapeutic effect.

BRIEF DESCRIPTIONS OF THE DRAWINGS

DETAILED DESCRIPTION

Figure 1:
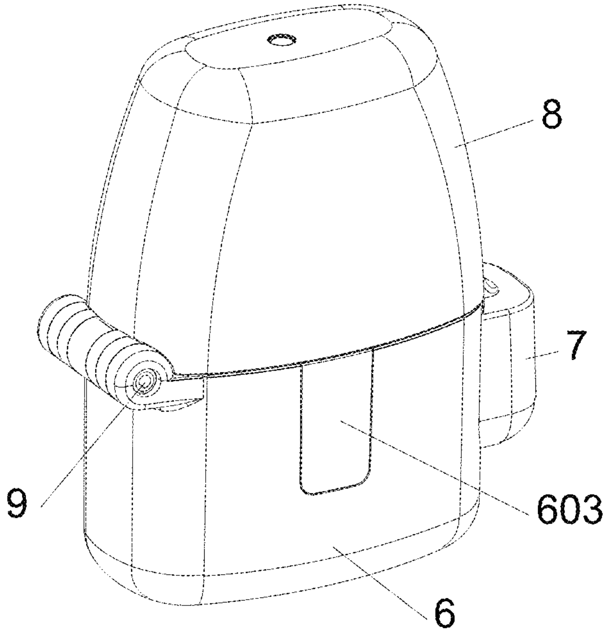
FIG. 1 is a schematic structural diagram of a powder inhalation device according to an embodiment of the present invention.

Example implementations will now be described more fully with reference to the accompanying drawings. However, the example implementations can be implemented in a variety of forms and should not be construed as being limited to the implementations set forth herein; rather, the provision of these implementations makes the present invention more thorough and complete, and the concepts of the example implementations are fully conveyed to those skilled in the art. In the figures, the same reference numerals indicate the same or similar structure, and thus their repeated description will be omitted.

The words expressing position and direction described in the present invention are all illustrated by taking the accompanying drawings as examples, but changes may be made as necessary and are included in the scope of protection of the present invention.

Example 1

Referring to FIGS. 1 to 5B, the present application discloses a powder inhalation device, which is mainly configured for pulmonary inhalation administration therapy. The powder inhalation device includes a carrier plate 1, a mouthpiece 2, a capsule chamber 3, and also includes an air intake slot 103.

Figure 2:
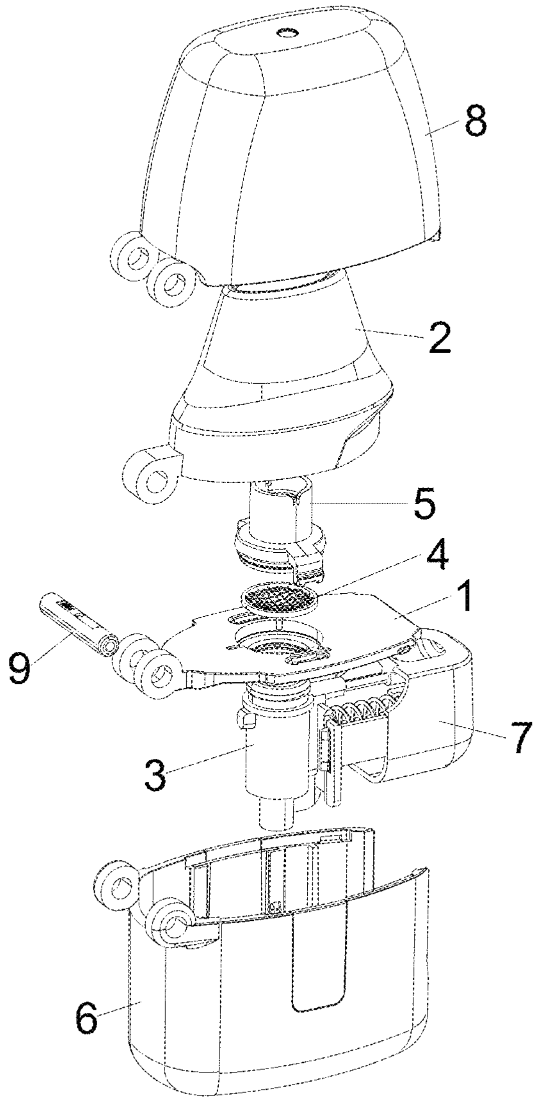
FIG. 2 is a schematic structural exploded view of a powder inhalation device according to an embodiment of the present invention.
Figure 3:
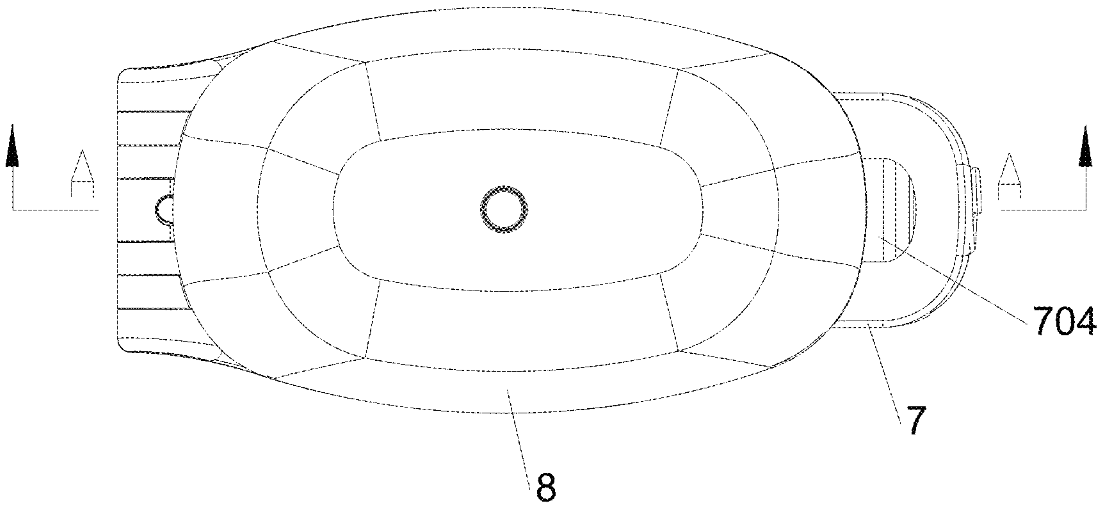
FIG. 3 is a top view of a powder inhalation device according to an embodiment of the present invention.
Figure 5A:
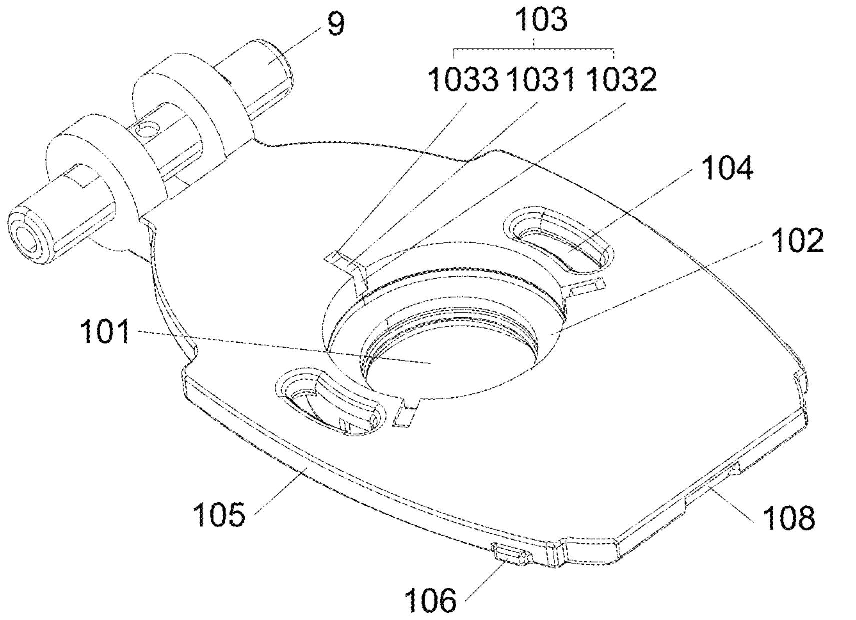
FIG. 5A is a schematic structural diagram of a carrier plate according to an embodiment of the present invention.

As shown in FIGS. 2 and 5A, the carrier plate 1 is an approximately elliptical flat plate, and a through hole 101 is provided on the support plate 1. For example, the through hole 101 is preferably located in the center of the carrier plate 1 and extends vertically through an upper surface and a lower surface of the carrier plate 1, so that a first airflow in the capsule chamber 3 can flow upward to the mouthpiece 2.

In addition, an annular groove 102 is provided at an outer periphery of the through hole 101, and the annular groove 102 may be arranged around the through hole 101, so that an annular step structure is formed between the annular groove 102 and the through hole 101 to facilitate the installation of a sieve mesh 4 and a sieve holder 5.

Figure 4A:
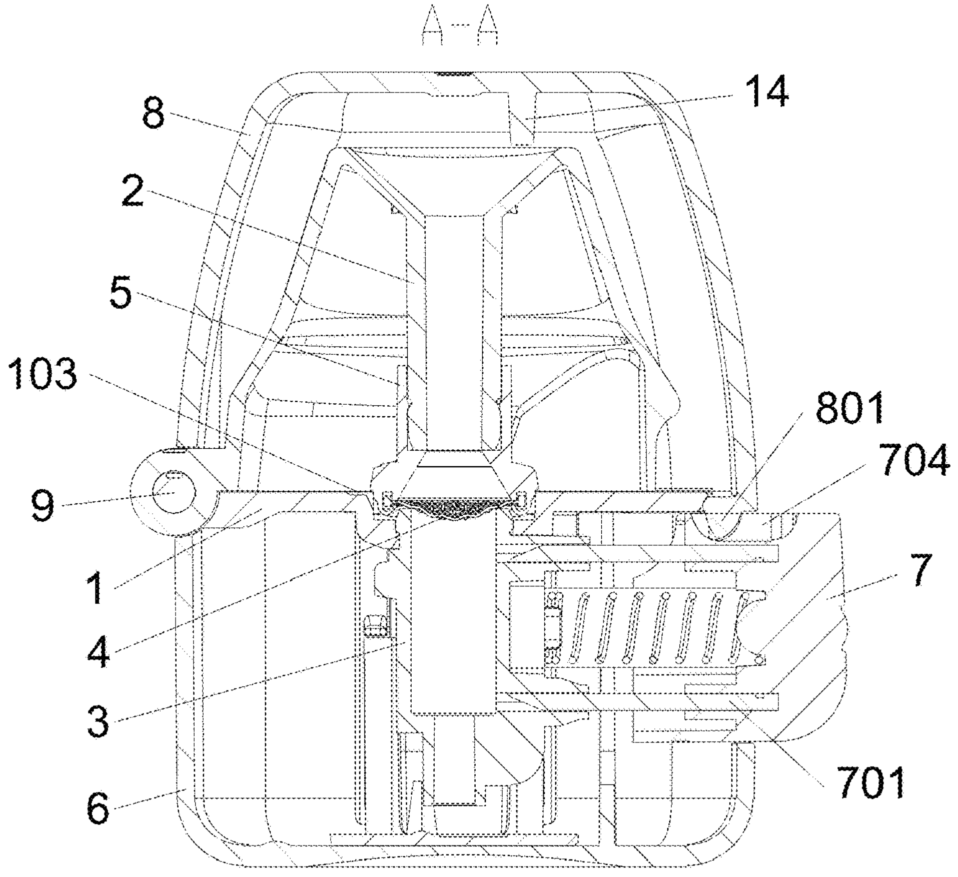
FIG. 4A is a cross-sectional view along A-A of FIG. 3.

As shown in FIGS. 2 and 4A, the mouthpiece 2 is substantially in the shape of a flat truncated cone, and the mouthpiece 2 is disposed above the carrier plate 1, wherein the mouthpiece 2 and the carrier plate 1 may be of a split structure or an integrated structure. Illustratively, one side of the mouthpiece 2 is hinged to one side of the carrier plate 1, thereby facilitating the opening or closing of the mouthpiece 2 to meet the requirements of medicament loading or cleaning, and improve the convenience of operation.

Also, the mouthpiece 2 is in communication with the through hole 101. Specifically, the mouthpiece 2 has a suction channel (located at the center of the mouthpiece 2) disposed in a height direction, and the suction channel has one end in coaxial communication with the through hole 101, and the other end provided with a tapered hole to facilitate powder dispersion and release.

As also shown in FIGS. 2 and 4A, the capsule chamber 3 has a substantially tubular structure, the capsule chamber 3 is disposed under the carrier plate 1, and the capsule chamber 3 and the carrier plate 1 may likewise be of a split structure or an integrated structure. For example, the top of the capsule chamber 3 is provided with a snap-in structure adapted to the through hole 101, so as to facilitate the removal of the capsule chamber 3 for a cleaning operation.

Figure 4B:
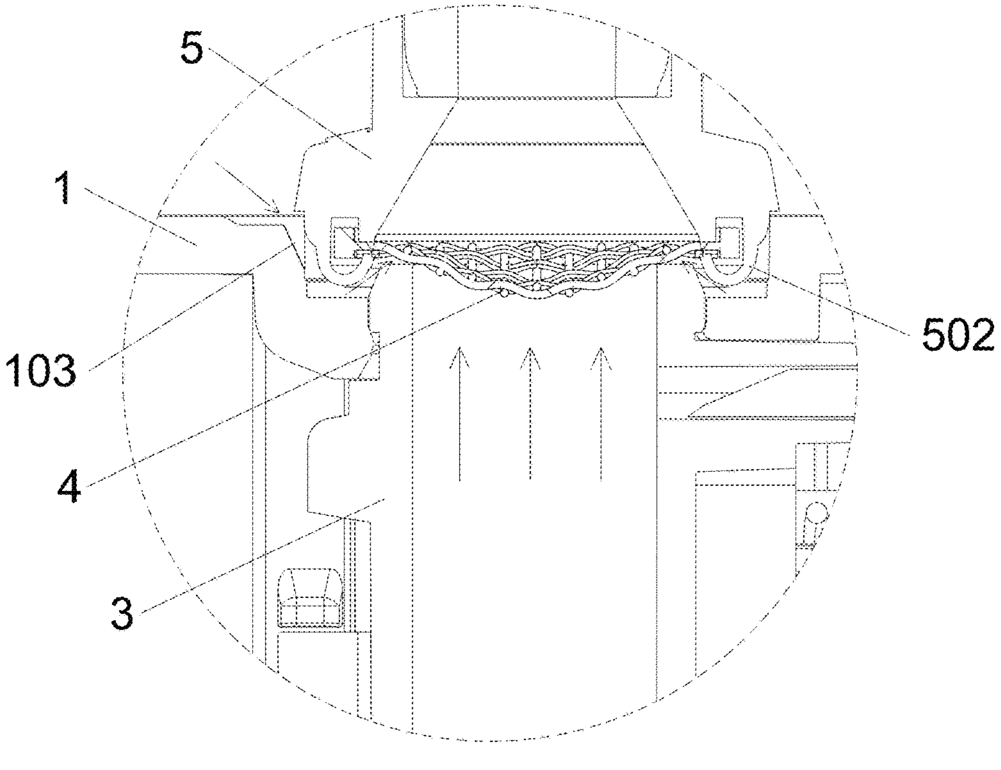
FIG. 4B is a partial enlarged view showing a place where an air intake slot is connected to a capsule chamber of FIG. 4A.

In addition, the capsule chamber 3 is in communication with the through hole 101, and the capsule chamber 3 is also in communication with the outside atmosphere for inhalation of the first airflow (see FIGS. 4A and 4B). Specifically, the capsule chamber 3 has a stepped through hole which is larger at the top and smaller at the bottom, so as to fulfill the function of placing a target strong capsule and allowing a first airflow to convey the medicament.

Figure 5B:
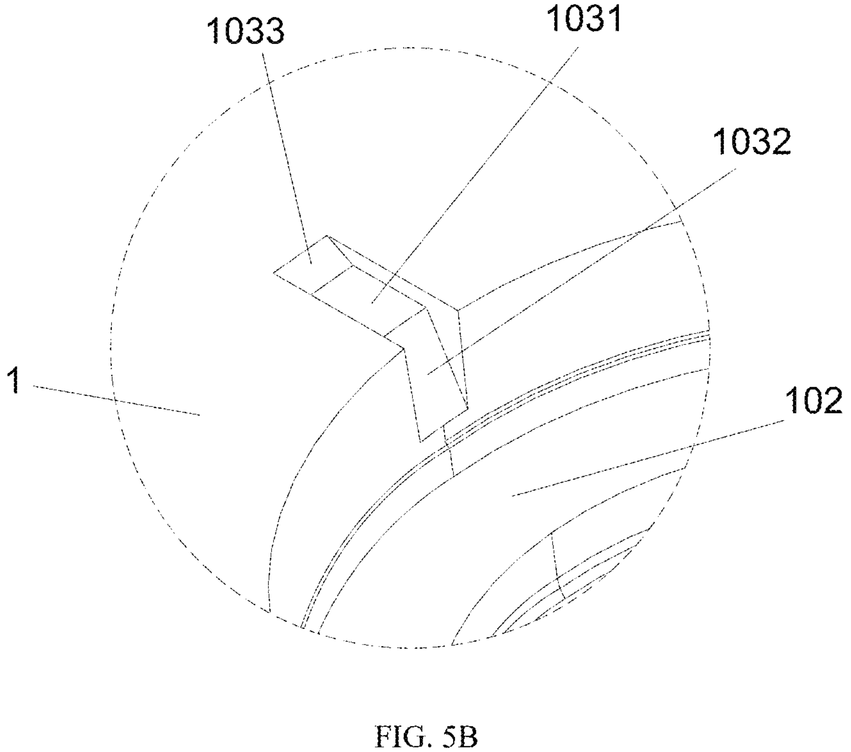
FIG. 5B is a partial enlarged view of a portion of the air intake slot in FIG. 5A.

As shown in FIGS. 5A and 5B, at least one air intake slot 103 is provided at the outer periphery of the through hole 101. For example, three air intake slots 103 are uniformly provided at the outer periphery of the through hole 101, and an included angle between adjacent air intake slots 103 is 120°, so as to achieve a stable intake airflow, i.e., a second airflow.

Each air intake slot 103 includes a horizontal slot section 1031 and an oblique slot section 1032. The horizontal slot section 1031 is located on the upper surface of the carrier plate 1, the oblique slot section 1032 is located on a sidewall of the annular groove 102, and the horizontal slot section 1031 is connected to the oblique slot section 1032, so that the second airflow drawn from the air intake slot 103 can create a turbulent flow at the annular groove 102 (see FIG. 4B).

When in use, a patient inhales from the mouthpiece 2, powder in the capsule chamber 3 may be transported upward under the action of the first airflow, and the powder drawn out from the capsule chamber 3 is subjected to the second airflow drawn in from the air intake slot 103, so that the turbulent flow is created near the annular groove 102, and the turbulent force of the turbulent flow will be large, allowing the powder to be sufficiently dispersed, thereby improving the effect of inhalation administration.

The above-mentioned turbulent flow generally refers to turbulence, which is a flow state of a fluid. When the flow rate of the fluid is small, the fluid flows in distinct layers without mixing with each other, which is called as a laminar flow or a streamline flow; when the flow rate is gradually increased, streamlines of the fluid begins to exhibit wavy oscillations, the frequency and amplitude of the oscillations increase with the flow rate, and this flow condition is called as a transitional flow; and when the flow rate increases to a sufficiently high level, the streamlines become no longer clearly distinguishable, and there are many small vortices in a flow field, which is called as a turbulent flow, a chaotic flow, or turbulence. The turbulent flow in the vicinity of the annular groove 102 in this application corresponds to the third case.

In addition, since the air intake slot 103 is provided on the sidewall of the annular groove 102 rather than on a hole wall of the through hole 101, no structural damage is caused to the through hole 101, which avoids an operating obstacle caused by weakening of a connecting force between the capsule chamber 3 and the carrier plate 1, and improves the reliability of the device.

It should be noted that in the above-mentioned solution, an air intake amount of the air intake slot 103 depends on the sum of surface areas of the horizontal slot section 1031 and the oblique slot section 1032 and an included angle between the horizontal slot section 1031 and the oblique slot section 1032. The sum of the surface areas of the horizontal slot section 1031 and the oblique slot section 1032 is positively correlated to the air intake amount of the air intake slot 103, that is, the larger the surface areas of the horizontal slot section 1031 and the oblique slot section 1032, the greater the air intake amount of the corresponding air intake slot 103. In addition, the included angle between the horizontal slot section 1031 and the oblique slot section 1032 is negatively correlated to the air intake amount of the air intake slot 103, that is, the smaller the included angle between the horizontal slot section 1031 and the oblique slot section 1032, the greater the air intake amount of the corresponding air intake slot 103. By regulating the surface area and/or included angle of the two, the air intake amount can be accurately controlled, thus adjusting the turbulent force of the turbulent flow, and ensuring that the powder can be fully dispersed.

The sum of the surface areas of the horizontal slot section 1031 and the oblique slot section 1032 is too small and the included angle is too large, resulting in an insufficient air intake amount and having difficulty in creating an effective turbulent flow in the vicinity of the annular groove 102. As the sum of the surface areas of the horizontal slot section 1031 and the oblique slot section 1032 is too large, and the included angle is too small, a smooth upward transport of the powder is affected. To this end, in some embodiments, the sum of the surface areas of the horizontal slot section 1031 and the oblique slot section 1032 ranges from 2.65 $mm^2$-2.95 $mm^2$, the included angle between the horizontal slot section 1031 and the oblique slot section 1032 ranges from 110°-120°, and the intensity of the turbulent flow formed by the confluence of the second airflow and the first airflow can meet the design requirements within this parameter range.

Further, as shown in FIG. 5, the air intake slot 103 further includes a draft slot section 1033, the draft slot section 1033 being obliquely disposed on the upper surface of the carrier plate 1, and being located at an end of the horizontal slot section 1031 away from the oblique slot section 1032. In general, the draft slot section 1033, the horizontal slot section 1031 and the oblique slot section 1032 are integrally formed, and the draft slot section 1033 is designed to facilitate the demolding of the air intake slot 103.

Example 2

Referring to FIGS. 1 to 6, embodiment 2 is based on the structure of the powder inhalation device of embodiment 1, and the differences therebetween are as follow: the sieve mesh 4 is disposed between the mouthpiece 2 and the carrier plate 1, and the sieve mesh 4 is located at the through hole 101. The sieve mesh 4 is configured to intercept large particles of powder that have not been broken up and to screen out powder with suitable particle sizes, so as to ensure the quality and effectiveness of the administration therapy.

In some embodiments, the sieve mesh 4 is substantially of a downwardly concave curved configuration, thereby increasing the filtration area so that the powder has a sufficient pass rate. The sieve mesh 4 can be made of stainless steel, is clean, hygienic and corrosion-resistant, and can effectively avoid contamination of inhaled powder. Further, it is also possible to provide a non-toxic anti-sticking layer on the surface of the sieve mesh 4 to reduce powder accumulation and to prevent the sieve mesh 4 from being blocked and affecting normal use.

Figure 6:
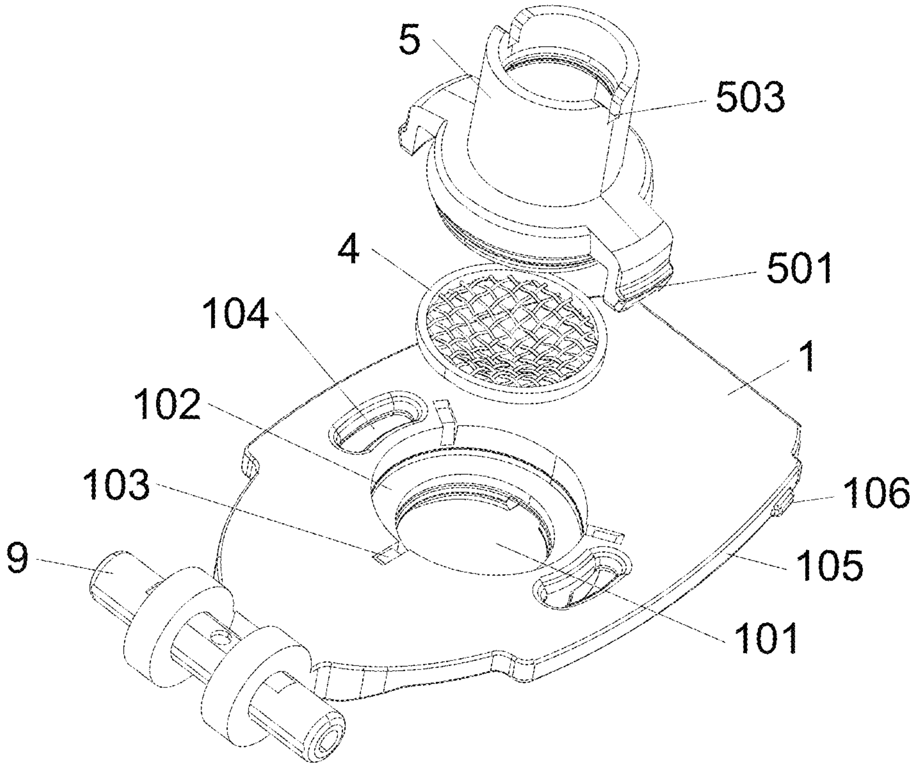
FIG. 6 is a schematic structural diagram showing the connection of the carrier plate to a sieve holder according to an embodiment of the present invention.

As shown in FIGS. 2, 4 and 6, in some embodiments, the sieve holder 5 is provided in the mouthpiece 2, and the sieve mesh 4 is provided in the sieve holder 5. The sieve holder 5 has a generally T-shaped structure and is connected to the mouthpiece 2 and the carrier plate 1, respectively. Specifically, the top of the sieve holder 5 is connected to the suction channel of the mouthpiece 2, the bottom of the sieve holder 5 is connected to the carrier plate 1, and the sieve holder is partially disposed in the annular groove 102 and forms an airflow channel with the air intake slot 103, so that the second airflow outside the sieve holder 5 can pass through the airflow channel into the vicinity of the annular groove 102 to create the turbulent flow.

Illustratively, at least two first snap-fits 501 are provided at an outer periphery of the sieve holder 5, and the carrier plate 1 is provided with at least two first snap-fit grooves 104. The first snap-fit grooves 104 correspond to and mate with the first snap-fits 501, and the sieve holder 5 is snap-fitted and secured to the carrier plate 1 by the first snap-fits 501 and the first snap-fit grooves 104, so that the sieve holder 5 is detachably mounted, and the sieve mesh 4 is easily cleaned or replaced.

Figure 17:
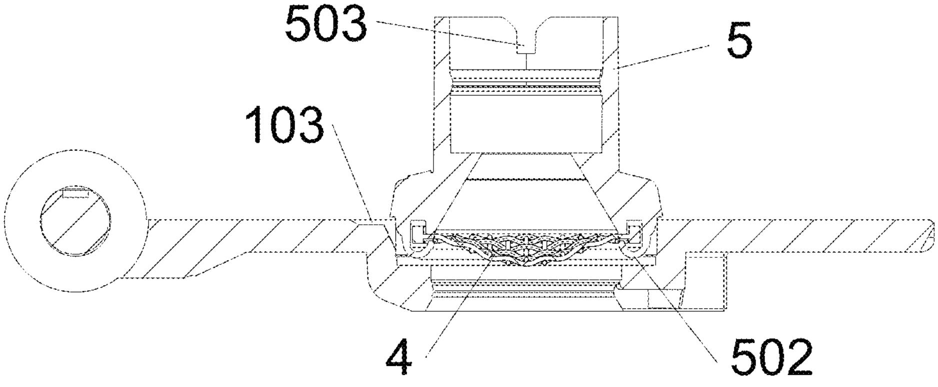
FIG. 17 is a schematic structural diagram showing the connection of a sieve mesh to a sieve holder according to an embodiment of the present invention.

The sieve mesh 4 and the sieve holder 5 described above may be of a split or integrated structure. In some embodiments, as shown in FIG. 17, the bottom of the sieve holder 5 has a fixing portion 502 for fixing the sieve mesh 4, before the sieve mesh 4 is loaded, the fixing portion 502 is in a vertical state (not shown), and after the sieve mesh 4 is loaded, the fixing portion 502 is heat-melted and bent into a hook shape and clamps and fixes the sieve mesh 4.

Figure 20:
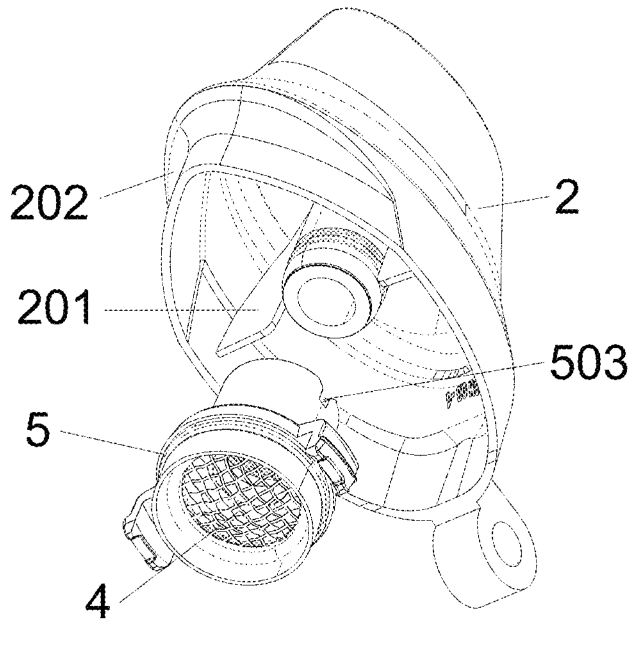
FIG. 20 is a schematic structural exploded view showing the connection of a mouthpiece to a sieve according to an embodiment of the present invention.

As shown in FIG. 20, in some embodiments, a support rib 201 is also provided in the mouthpiece 2. For example, two support ribs 201 are provided and are symmetrically distributed on two sides of the suction channel to enhance the stability of the structure of the suction channel. In addition, a guide slot 503 is provided at the top of the sieve holder 5. For example, two guide slots 503 are provided and are symmetrically distributed on two sides of the sieve holder 5, and the guide slots 503 are in one-to-one correspondence with the support ribs 201. Thus, when the sieve holder 5 is assembled with the mouthpiece 2, it can be guided by the cooperation of the guide slots 503 with the support ribs 201, to ensure the accuracy of the positions of the mouthpiece 2 and the sieve holder 5.

Example 3

Referring to FIGS. 1 to 9, embodiment 3 is based on the structure of the powder inhalation device of embodiment 1 or embodiment 2, and the differences therebetween are: the powder inhalation device further includes a lower shell 6.

The top of the lower shell 6 is open, the carrier plate 1 is hinged to the lower shell 6 and is snap-fitted to the top of the lower shell 6, which enables the carrier plate 1 to be closed/opened under an external force, and facilitates cleaning the lower shell 6 and the capsule chamber 3. The capsule chamber 3 is housed inside the lower shell 6 to avoid contamination.

Since the lower shell 6 is an injection molded part, a lower shell 6 of an existing powder inhalation device is generally manufactured by injection molding, and an inner shell 602 is injection molded into the interior of an outer shell 601 during production, thereby forming an integrated lower shell 6. However, the method has the disadvantages of a low production efficiency and a high replacement cost of the entire component.

Figure 7:
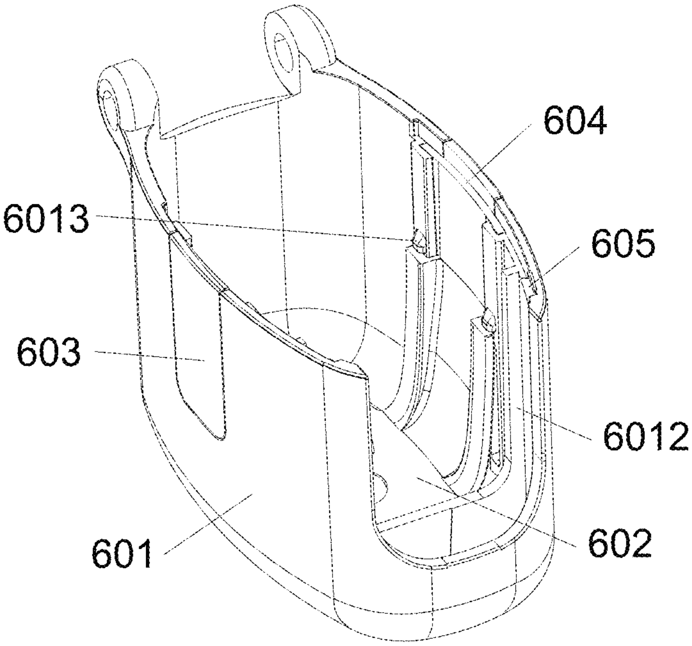
FIG. 7 is a schematic structural diagram of a lower shell according to an embodiment of the present invention.
Figure 8:
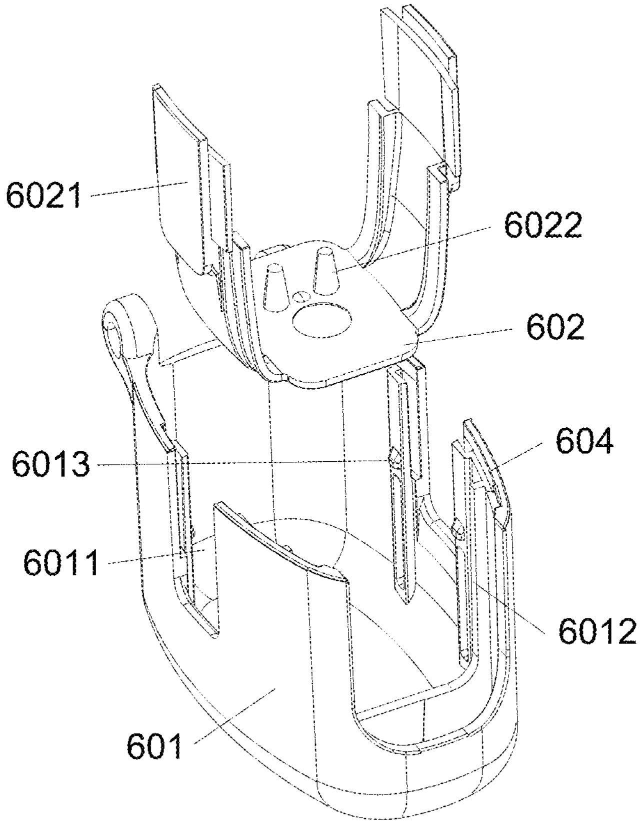
FIG. 8 is a schematic structural exploded view of FIG. 7.

Thus, as shown in FIGS. 7 and 8, in some embodiments, the lower shell 6 is designed as a split structure, the lower shell 6 includes an outer shell 601 and an inner shell 602, and the outer shell 601 and the inner shell 602 are separately manufactured and then assembled to form the desired lower shell 6. Compared with a conventional integrated lower shell 6, a secondary injection molding process is not required, the production efficiency is relatively high, and once the lower shell 6 is damaged, replacement of the corresponding outer shell 601 or inner shell 602 is possible without the need for a complete replacement, thereby achieving low maintenance costs.

Illustratively, the outer shell 601 is provided with an opening 6011 on each side of the capsule chamber 3 (both sides corresponding to a width direction of the powder inhalation device), the opening 6011 being a U-shaped opening with an open top, and the openings 6011 on both sides of the outer shell 601 can be arranged symmetrically or asymmetrically, as long as the capsule chamber 3 inside the lower shell 6 can be seen. In addition, notch structures

6012 are symmetrically provided on both sides of the opening 6011, and each of the notch structures 6012 is composed of an L-shaped plate-like part integrally formed with the outer shell 601, and can serve as a guide to facilitate the installation of the inner shell 602.

The inner shell 602 is of a generally U-shaped structure, and has upwardly extending side panels 6021 on both sides (both sides corresponding to the width direction of the powder inhalation device), and the side panels 6021 are at least partially engaged with the notch structures 6012 to secure the inner shell 602 within the outer shell 601. At the same time, part of the side panel 6021 forms a viewing window 603 at the corresponding opening 6011, which is configured to view the situation of the capsule chamber 3 and is convenient for the patient to use. It should be noted that at least a portion of the side panel 6021 that is embedded in the opening 6011 is transparent, to ensure that the patient can see the interior of the lower shell 6 through the viewing window 603, and that the inner shell 602 can be more rigid than the outer shell 601, thereby strengthening the structure of the outer shell 601 to avoid deformation and affecting use.

Further, as shown in FIG. 8, the notch structure 6012 is provided with a limit block 6013, which is integrally formed with the notch structure 6012 to restrict the position of the inner shell 602. Specifically, a downwardly sloping ramp structure is provided at the top of the limit block 6013 to facilitate smooth mounting of the inner shell 602 into the outer shell 601, and a limit surface is provided at the bottom of the limit block 6013 to limit upward movement of the inner shell 602, thereby restricting the position of the inner shell 602 and ensuring the stability and firmness of the inner shell 602 and the outer shell 601 after assembly.

In addition, an auxiliary column 6022 is provided at an inner bottom of the inner shell 602. For example, two auxiliary columns 6022 are provided, and are arranged side by side on one side of the capsule chamber 3. Taking FIG. 8 as an example, it is defined that two sides in the width direction of the powder inhalation device correspond to front and rear directions respectively, and two sides in a length direction correspond to left and right directions respectively. When the capsule chamber 3 is properly mounted, the auxiliary columns 6022 are located on the left side of the capsule chamber 3, and are configured to correct and position the capsule chamber 3, which can serve as a fool-proofing feature.

Figure 9:
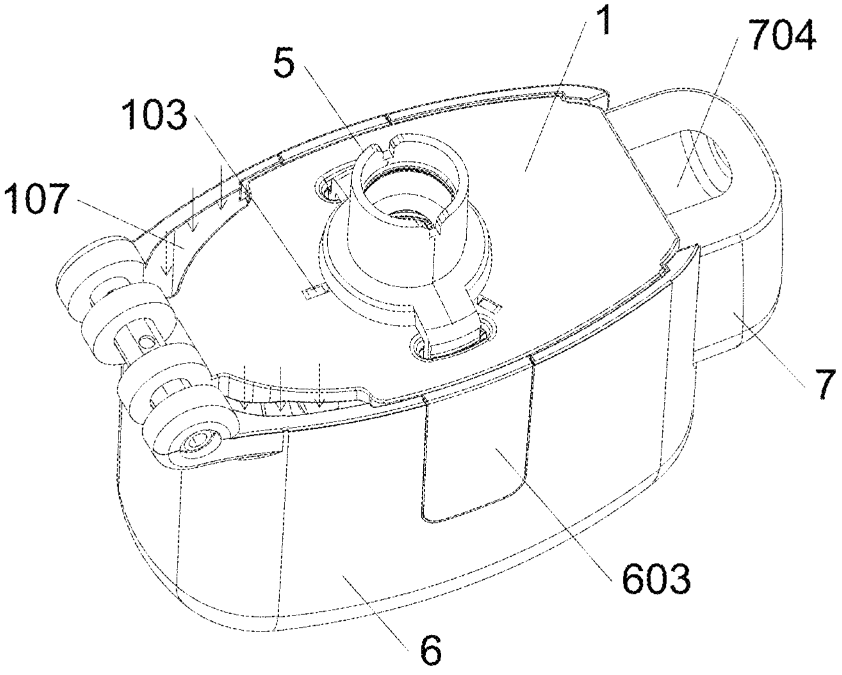
FIG. 9 is a schematic structural diagram showing the connection of the carrier plate to the lower shell according to an embodiment of the present invention.
Figure 10:
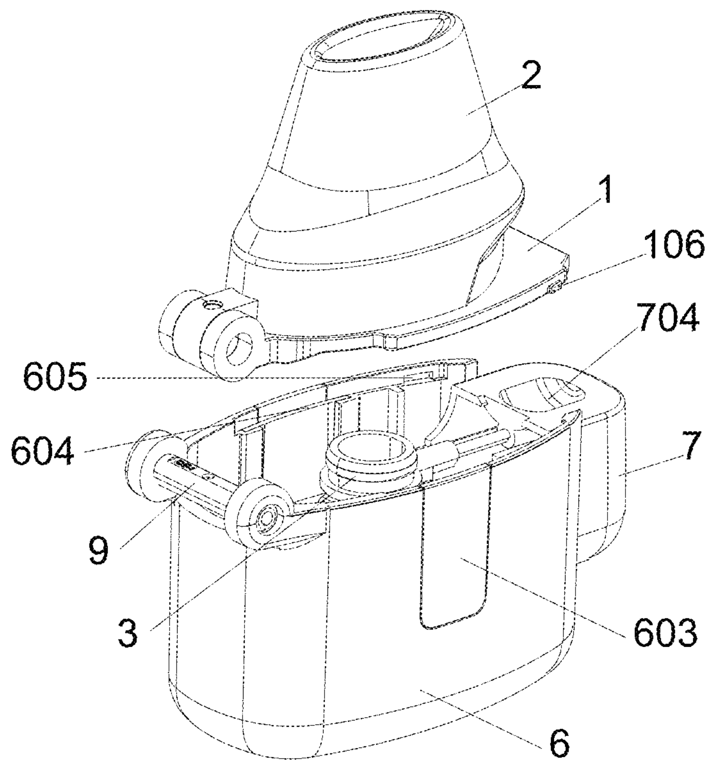
FIG. 10 is a partial schematic structural exploded view of the powder inhalation device according to an embodiment of the present invention.

As shown in FIGS. 7 and 9 to 10, in some embodiments, steps 604 are provided on two sides of the top of the lower shell 6, the steps 604 extends in a length direction of the lower shell 6 and has an overall arc-shaped strip structure, and the step 604 is provided with a second snap-fit groove 605 at a hinge point away from the lower shell 6, thereby increasing the length of a moment arm of the second snap-fit groove 605 at a distance from the hinge point of the lower shell 6.

Flanges 105 are provided on both sides of the carrier plate 1, each flange 105 protrudes in a width direction of the carrier plate 1, and the flange 105 is provided with a second snap-fit 106 at a hinge point away from the carrier plate 1, where the flange 105 corresponds to and matches the step 604, and the second snap-fit 106 corresponds to and matches the second snap-fit groove 605.

The flange 105 is provided on the step 604 and is snap-fitted and fixed to the second snap-fit groove 605 by the second snap-fit 106, so that the carrier plate 1 is detachably connected to the lower shell 6. It should be noted that since one side of the carrier plate 1 is hinged to one side of the lower shell 6, a snap-fit connection being designed to be away from the hinge point can provide a better installation effect. However, it should be noted that the second snap-fit 106 is avoided from a corner area formed by the flange 105 and the carrier plate 1, because the corner area has high molding requirements for the second snap-fit 106, and the structural strength of the second snap-fit 106 is difficult to ensure.

As also shown in FIG. 9, in some embodiments, an air intake gap 107 is formed between the carrier plate 1 and the lower shell 6, and the air intake gap 107 is in communication with the bottom of the capsule chamber 3, such that the second airflow enters the capsule chamber 3 through the air intake gap 107, thereby providing a motive airflow required for powder transport. So that the powder in the capsule chamber 3 is drawn near the annular groove 102 through the first airflow and is mixed with the second airflow drawn from the air intake slot 103 to form a turbulent flow, and the powder is dispersed and then enters the suction channel of the mouthpiece 2.

Illustratively, two air intake gaps 107 are formed between the carrier plate 1 and the lower shell 6 at the hinge points, the two air intake gaps 107 being symmetrical about a centerline along a length direction of the carrier plate 1, and an area of each of the air intake gaps 107 is substantially larger than an area of the air intake slot 103, so as to ensure that the airflow entering the lower shell 6 is uniform and sufficient.

Example 4

Referring to FIGS. 1 to 11, embodiment 4 is based on the structure of the powder inhalation device of embodiment 3, and the differences therebetween are: The powder inhalation device further includes an operating mechanism 7 with a lancet 701.

Figure 11:
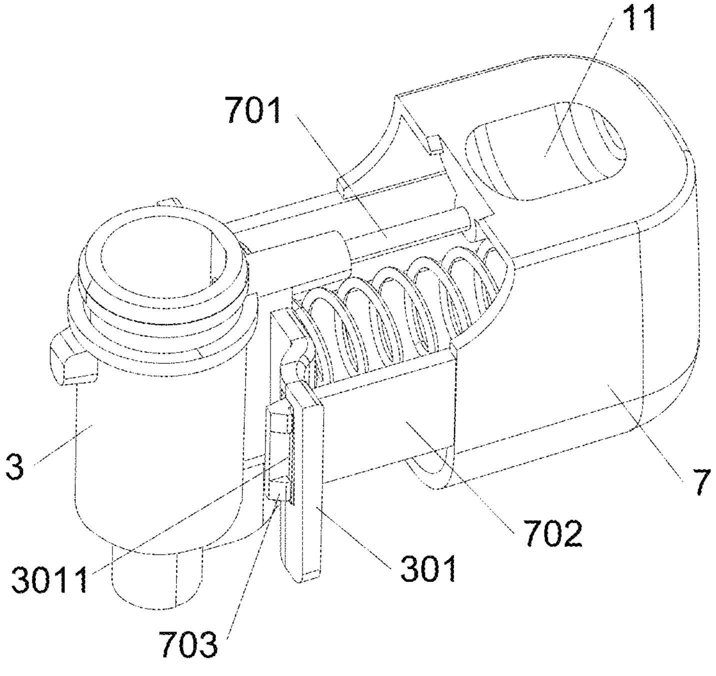
FIG. 11 is a schematic diagram of the cooperation of the capsule chamber with an operating mechanism according to an embodiment of the present invention.

The operating mechanism 7 is movably arranged on a sidewall of the lower shell 6, such as on a sidewall of a side of the lower shell 6 away from the hinge point. The operating mechanism 7 is configured as a dual function actuator, and in a first actuation, the operating mechanism may drive the upper shell 8 to open; and in a second actuation, the operating mechanism 7 may drive the lancet 701 to pierce a target capsule in the capsule chamber 3 to release the powder. As shown in FIG. 11, in some embodiments, the operating mechanism 7 includes guide plates 702 parallel to the lancet 701. For example, the guide plates 702 are distributed on both sides in a length direction of the lancet 701 to improve the smoothness of guide movement, and the guide plates 702 are integrally formed with the operating mechanism 7.

A guiding plate 301 is provided on a side of the capsule chamber 3 facing the operating mechanism 7, and the guiding plate 301 is in a vertical state and can be fixedly connected to the capsule chamber 3 or to the lower shell 6. In addition, the guiding plate 301 is formed with a guiding hole 3011 matching a corresponding one of the guide plates 702 such that the guide plate 702 is slidably inserted into the guiding hole 3011 to guide linear movement of the operating mechanism 7 and the lancet 701 and prevent deviation of the direction of movement during pressing, which in turn prevents the lancet 701 from being unable to accurately pierce the target capsule, and avoids even the possibility of the lancet 701 being bent or broken. Further, a backstop 703 is provided at an end of the guide plate 702 close to the capsule chamber 3, and the backstop 703 may form a stop on a side of the guiding plate 301 close to the capsule chamber 3, thereby preventing the guide plate 702 from completely disengaging from the guiding hole 3011, thus preventing the operating mechanism 7 from being separated from the lower shell 6, and achieving an anti-release function.

Figure 18:
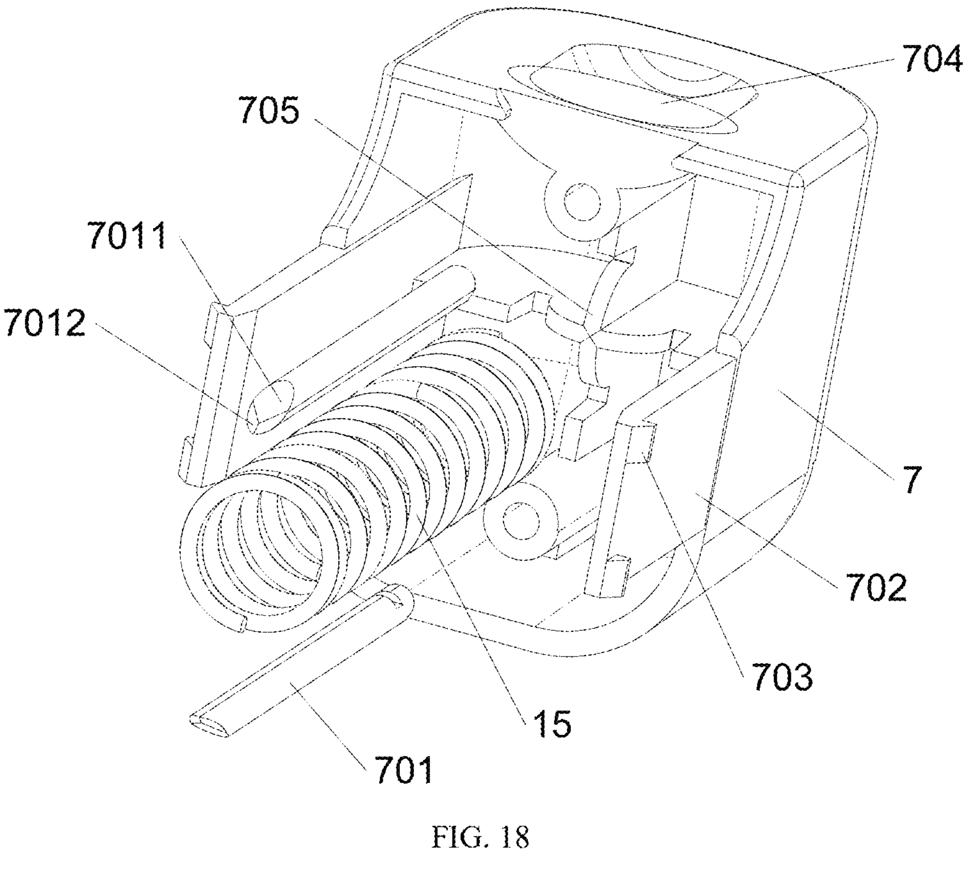
FIG. 18 is a schematic structural diagram showing the assembly of the operating mechanism with a spring according to an embodiment of the present invention.
Figure 19:
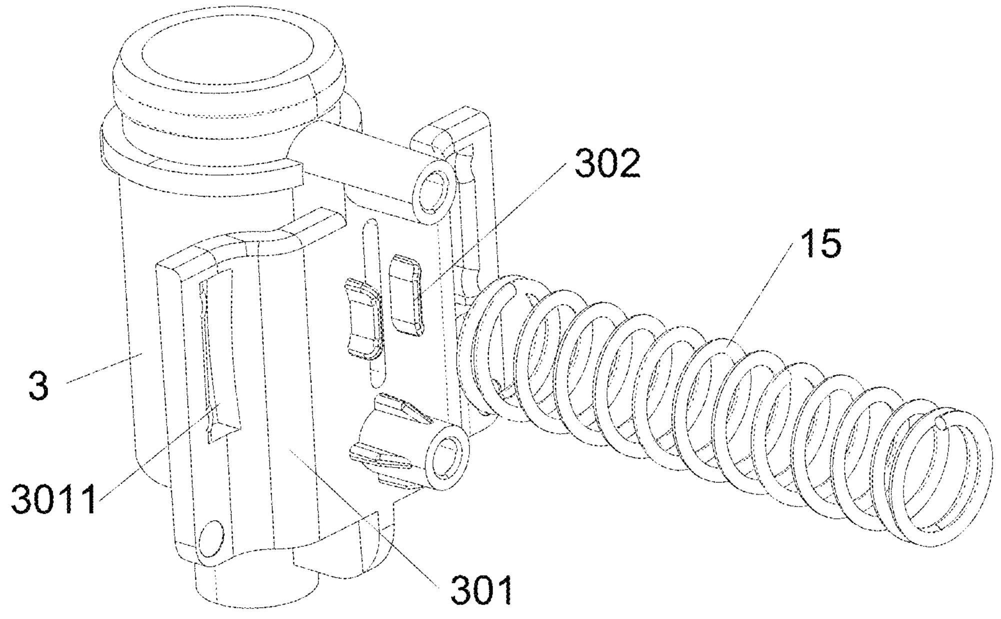
FIG. 19 is a schematic structural diagram showing the assembly of the capsule chamber and the spring according to an embodiment of the present invention.

As shown in FIGS. 18 and 19, in some embodiments, a spring 15 is arranged between the capsule chamber and the operating mechanism, and the spring 15 is configured to provide a resilient force such that the operating mechanism 7 can be reset after being pressed. A rib 302 is provided on the side of the capsule chamber 3 facing the operating mechanism 7, and the rib 302 is substantially in the shape of ") (", which can be integrally formed with the guiding plate 301. In addition, a cross-shaped protrusion 705 is provided on a side of the operating mechanism 7 facing the capsule chamber 3, and four sides of the cross-shaped protrusion 705 extend outward and form a reinforcing rib structure in the operating mechanism 7, thereby structurally reinforcing the operating mechanism 7.

Two ends of the spring 15 are fitted over the rib 302 and the cross-shaped protrusion 705, respectively, so as to achieve a positioning and fixing effect, ensuring the consistency of a telescopic path of the spring 15. As shown in FIG. 18, in some embodiments, an end of the lancet 701 close to the capsule chamber 3 is of a multifaceted structure, the multifaceted structure including a main oblique piercing surface 7011 and lateral piercing surfaces 7012 on two sides of the main oblique piercing surface 7011, which increases the strength of a needle tip of the lancet 701, and avoids deformation or breakage of the needle tip and then affecting a piercing operation. In short, if only the main oblique piercing surface 7011 extending to the tip is present, the needle tip of the main oblique piercing surface 7011 is thin and has a relatively fragile structure, and by providing the lateral piercing surfaces 7012 on both sides, a thickness of the needle tip is increased indirectly, so that the needle tip is not easily damaged, ensuring the stability of the piercing effect.

Example 5

Referring to FIGS. 1 to 13, embodiment 5 is based on the structure of the powder inhalation device of embodiment 4, and the differences therebetween are: the powder inhalation device also includes an upper shell 8.

The bottom of the upper shell 8 is open to cover the mouthpiece 2 and the carrier plate 1, one side of the upper shell 8 is hinged to the carrier plate 1, and the opening and closing of the upper shell 8 can be switched by flipping. In addition, a closure 801 is provided on the other side of the upper shell 8, and the closure 801 can cooperate with a boat-shaped recess 704 of the operating mechanism 7 and an interference surface 108 of the carrier plate 1, to achieve the functions of opening and locking upon closing of the upper shell 8.

The interference surface 108 is provided on a side of the carrier plate 1 close to the operating mechanism 7, and the interference surface 108 is an inclined surface and is specifically located at an edge of a side of the carrier plate 1 away from the hinge point. The interference surface 108 is configured to abut against the closure 801 so that the upper shell 8 is temporarily fixed to the carrier plate 1 after closure, and the interference surface 108 can be guided to slide upward under a certain external force, causing the upper shell 8 to open.

The boat-shaped recess 704 is provided at the top of the operating mechanism 7, the boat-shaped recess 704 resembles a hull-like shape and has arc-shaped surfaces at both ends for guiding the movement of the closure 801 so that it can enter or move out of the boat-shaped recess 704 more smoothly.

When the upper shell 8 is in a closed state, the closure 801 is located just inside the boat-shaped recess 704 and is held against the interference surface 108, and the range of interference between the two is preferably controlled to be 0.3-0.5 mm. Only when an acting force exerted by the boat-shaped recess 704 on the closure 801 is larger than an interference force between the closure 801 and the interference surface 108, the closure 801 can be disengaged from the interference surface 108 and automatically open the upper shell 8, thereby unlocking the closure 801 from the carrier plate 1, which prevents a covering function of the upper shell 8 from failing due to the operating mechanism 7 being accidentally touched.

It should be noted that the acting force exerted by the boat-shaped recess 704 on the closure 801 needs to be less than a snap-fit force between the carrier plate 1 and the lower shell 6 to ensure that when the upper shell 8 is opened, the carrier plate 1 is not separated from the lower shell 6.

Figure 12:
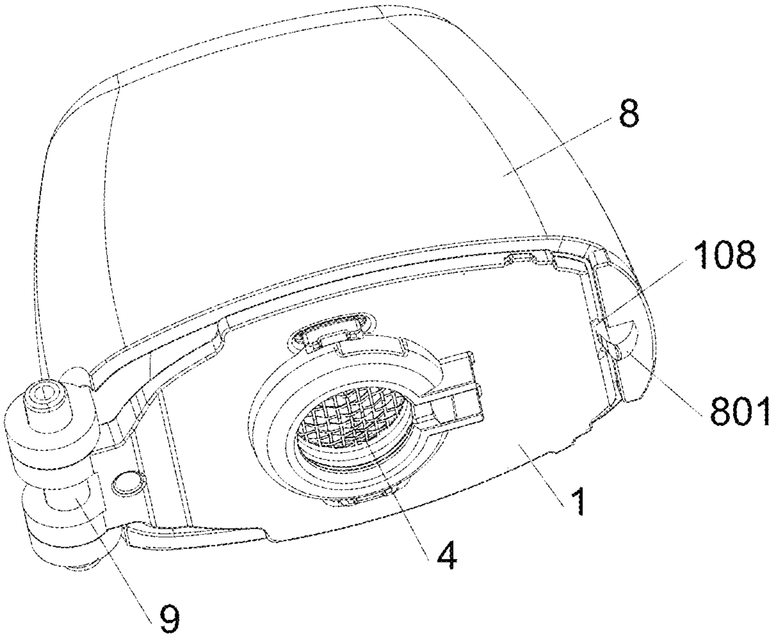
FIG. 12 is a schematic structural diagram showing the connection of the carrier plate to an upper shell according to an embodiment of the present invention.
Figure 13:
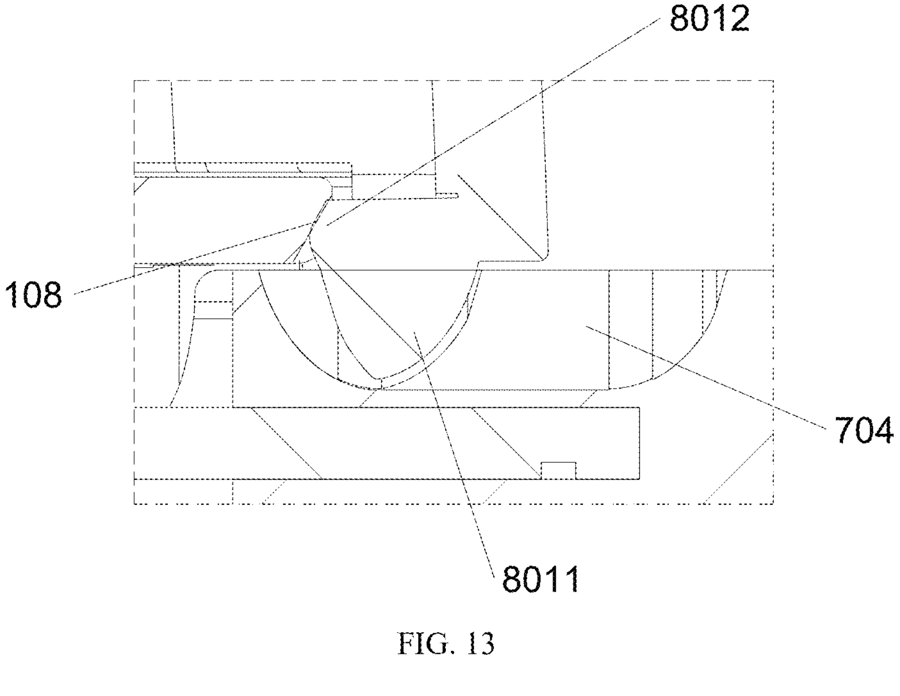
FIG. 13 is a partial enlarged view showing a place where the operating mechanism of FIG. 4A cooperates with an upper cover.

As shown in FIGS. 12 to 13, in some embodiments, the closure 801 is a special-shaped structural member, and the closure 801 includes a guide portion 8011 and an interference portion 8012 arranged in sequence from bottom to top. The guide portion 8011 has a generally Lello triangular structure with first and second arc surfaces of different radians on inner and outer sides. An inclined abutment surface is provided on a side of the interference portion 8012 close to the interference surface 108, and the abutment surface is connected in arc transition with the first arc surface inside the guide portion 8011 and is capable of being held against the interference surface 108.

When the upper shell 8 is closed, the first arc surface inside the guide portion 8011 first contacts the carrier plate 1 and guides the abutment surface of the interference portion 8012 to the interference surface 108 of the carrier plate 1 to effect a colliding fixation, and at this time the guide portion 8011 is located just inside the boat-shaped recess 704. When the upper shell 8 is opened, the operating mechanism 7 is driven under pressing by the patient, the boat-shaped recess 704 first contacts the second arc surface outside the guide portion 8011, and the second arc surface transmits the acting force to the interference portion 8012, until the abutment surface of the interference portion 8012 disengages from the interference surface 108 of the carrier plate 1, thereby allowing the closure 801 to move completely out of the boat-shaped recess 704.

As shown in FIG. 13, in some embodiments, an included angle between the interference surface 108 and a horizontal plane is 50-70°. If the included angle between the interference surface 108 and the horizontal plane is less than 50°, the interference surface 108 has too much interference against the closure 801, causing difficulty in opening the upper shell 8, which has an inconvenient effect on the operation; and if the included angle between the interference surface 108 and the horizontal plane is greater than 70°, the interference surface 108 is difficult to effectively resist interference, and the upper shell 8 is easily opened due to errors and is difficult to play an effective protective effect.

Preferably, the included angle between the interference surface 108 and the horizontal plane is 55-65°, especially when the included angle between the interference surface 108 and the horizontal plane is 60°, the interference between the two is better. Of course, in some other embodiments, it is also possible to enable the included angle between the interference surface 108 and the horizontal plane to be greater than or equal to 70° by providing a coarse friction layer (not shown) on the interference surface 108.

Example 6

Referring to FIGS. 1 to 2, in the powder inhalation device of the present embodiment, the carrier plate 1, the mouthpiece 2, the lower shell 6 and the upper shell 8 are connected by a hinge pin 9, the overall structure is simple and compact, and the opening and closing of the components is easy to operate.

Taking FIG. 1 as an example, the hinge pin 9 is located on one side in the length direction of the powder inhalation device, the carrier plate 1, the mouthpiece 2, the lower shell 6 and the upper shell 8 are each provided with corresponding flipping ears, which may be ring-shaped or C-shaped, to ensure that the ears are adapted to the hinge pin 9 and may drive the respective parts to rotate freely around the pin.

Further, as shown in FIG. 4A, a pressing rib 14 is provided at an inner top of the upper shell 8, a lower end of the pressing rib 14 is held against a top end of the mouthpiece 2, preferably against a side of the top end of the mouthpiece 2 away from the hinge point.

When the upper shell 8 is flipped and closed, the unclosed mouthpiece 2 can be flipped in the same direction under the action of the pressing rib 14 until it is completely closed on the carrier plate 1, thereby preventing the mouthpiece 2 from not being tightly closed due to a human error, and avoiding powder leakage or contamination in the capsule chamber 3, which can provide better insurance measures.

In addition, as also shown in FIG. 20, the mouthpiece 2 is provided with a recessed area 202 on a side away from the hinge pin 9 so that the patient may grasp the mouthpiece 2 and easily open or close the mouthpiece 2.

Example 7

Figure 14:
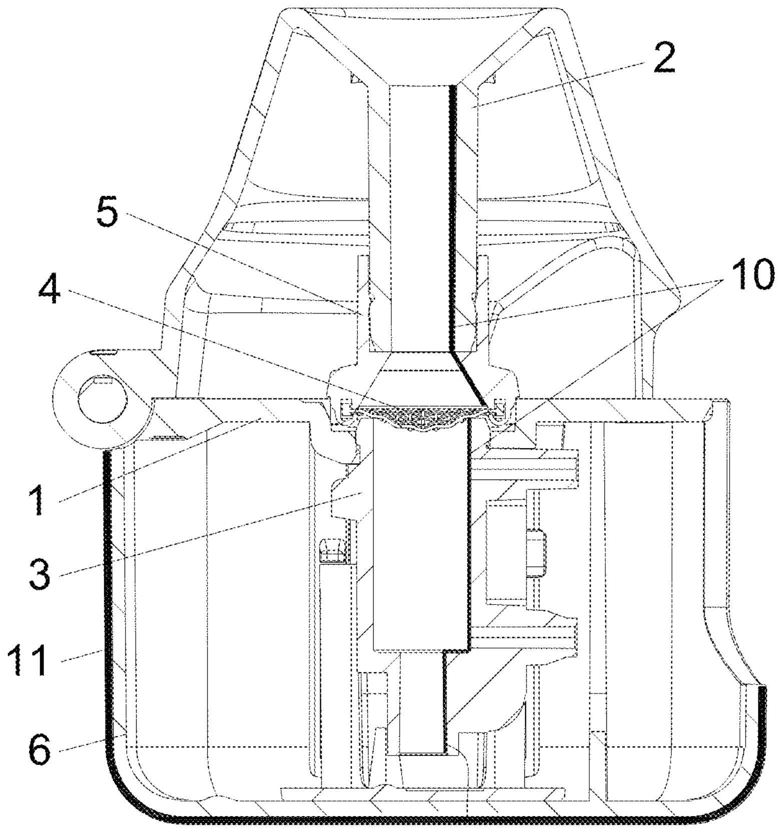
FIG. 14 is a schematic structural diagram of a first electrostatic removal method of the powder inhalation device according to an embodiment of the present invention.
Figure 15:
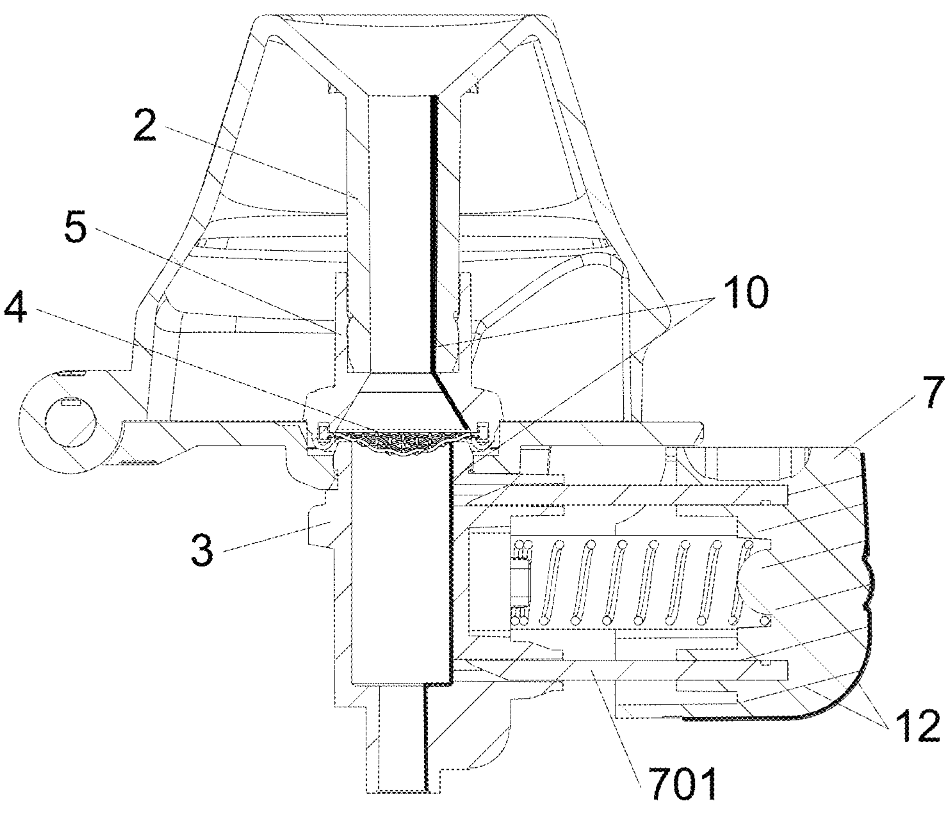
FIG. 15 is a schematic structural diagram of a second electrostatic removal method of the powder inhalation device according to an embodiment of the present invention.

Referring to FIGS. 14 to 15, embodiment 7 is based on the structure of the powder inhalation device of embodiment 3 to 6, and the differences therebetween are: An inner wall of the mouthpiece 2 (in particular an inner wall of a suction channel) and an inner wall of the capsule chamber 3 are provided with a first conductive layer 10, and the first conductive layer 10 may be a metal layer, such as an aluminum layer, a copper layer, a silver layer, etc., and may also be a plastic conductive layer. An outer surface of the lower shell 6 is provided with a second conductive layer 11, and the second conductive layer 11 is similar to the first conductive layer 10, so that a conductive function can be realized.

The first conductive layer 10 is electrically connected to the second conductive layer 11, such as by means of a wire or a plated hole lamp, so that static electricity generated by the use of the powder inhalation device is conducted out through a human body, so as to eliminate the static electricity, and prevent the powder from being deposited in the mouthpiece 2 and the capsule chamber 3 due to electrostatic charge adsorption, and being unable to be released (the situation of electrostatic adsorption is very serious when the size of powder particles is in a micrometer or nanometer range), causing the dose of powder inhaled into the patient's body is not accurate enough, and affecting a powder utilization rate and a therapeutic effect.

It should be noted that the first conductive layer 10 provided on the inner wall of the capsule chamber 3 should, as far as possible, avoid completely covering the capsule chamber 3, so as not to affect the patient's viewing of the situation in the capsule chamber 3 through the viewing window 603. Illustratively, the first conductive layer 10 on the inner wall of the capsule chamber 3 may be in a grid-like arrangement, leaving a visible partial area.

In some embodiments, the inner shell 602 and the capsule chamber 3 are of a transparent plastic material to meet the requirements for viewing. The outer shell 601 is made of a non-transparent plastic material, is configured to cover most of internal parts of the shell, and improves the aesthetics of the shape.

The second conductive layer 11 and the inner shell 602 form a cross structure, i.e., the inner shell 602 is arranged along the width direction of the powder inhalation device, the second conductive layer 11 is arranged along the length direction of the powder inhalation device, the second conductive layer 11 is preferably a hard metal layer, such as a steel layer, which can improve the texture of the powder inhalation device while the structural strength of the lower shell 6 is strengthened.

Example 8

Referring to FIG. 15, embodiment 8 is based on embodiment 4 to 6, and the differences therebetween are: An inner part of the mouthpiece 2 and an inner wall of the capsule chamber 3 are provided with a first conductive layer 10, and the first conductive layer 10 is the same as that in embodiment 7, which will not be described in detail here.

The lancet 701 is a conductive lancet, and which may be a metal lancet, such as a steel lancet, having strong rigidity and conductive properties.

A third conductive layer 12 is provided on a surface of the operating mechanism 7, or the inside of the operating mechanism 7 is provided with a third conductive layer 12 extending to the outside, and the third conductive layer 12 is preferably a hard metal layer, such as a steel layer.

The first conductive layer 10 is electrically connected to the third conductive layer 12 via the lancet 701, so that static electricity generated by the use of the powder inhalation device is conducted out through the human body, avoiding the effect of electrostatic charge on powder adsorption.

In contrast to embodiment 7, an electrostatic discharge path is different in this embodiment, the static electricity generated by the use of the inhalation device is transferred to the human body via the conductive lancet 701 and the inside of the operating mechanism 7 or an outer surface of the operating mechanism 7, finally realizing static elimination by grounding. In this embodiment, the third conductive layer 12 may strengthen the structure of the operating mechanism 7, and may also be more uniformly stressed, thereby making it more stable when piercing the target capsule. In some embodiments, the lancet 701 may be integrally formed with the third conductive layer 12 before injection molding with the operating mechanism 7.

Further, the third conductive layer 12 may form a non-slip structure (not shown) on the operating mechanism 7. For example, the third conductive layer 12 on the surface of the operating mechanism 7, or the third conductive layer 12 extending from the inside of the operating mechanism 7 to the outside is formed into an anti-slip pattern, which not only conducts the static electricity, but also has an anti-slip effect.

Example 9

Figure 16:
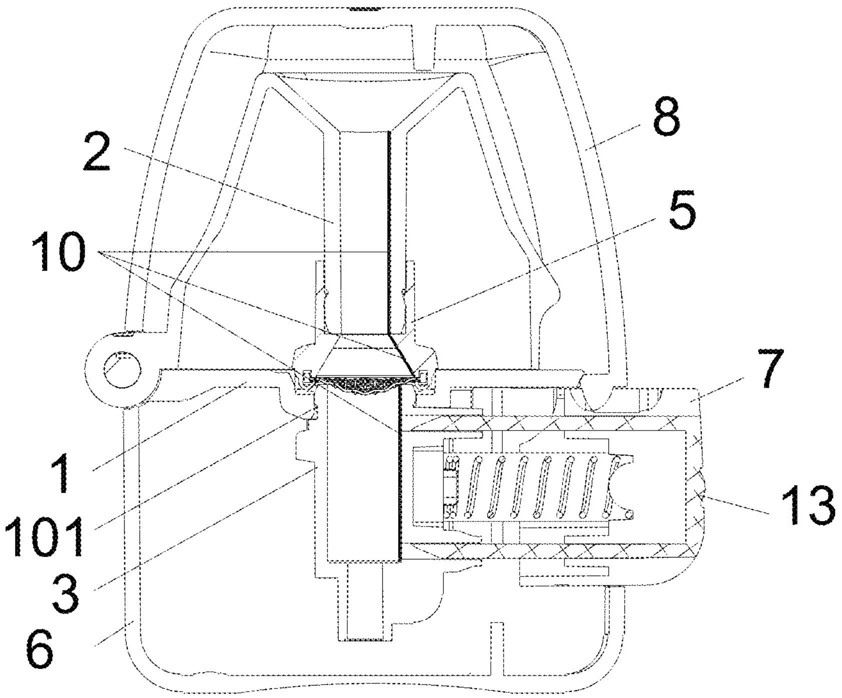
FIG. 16 is a schematic structural diagram of a third electrostatic removal method of the powder inhalation device according to an embodiment of the present invention.

Referring to FIG. 16, embodiment 9 is based on embodiment 4 to 6, and the differences therebetween are: An inner part of the mouthpiece 2 and an inner wall of the capsule chamber 3 are provided with a first conductive layer 10, and the first conductive layer 10 is the same as that in embodiment 7, which will not be described in detail here.

The lancet 701 is a non-conductive lancet extending to the surface of the operating mechanism 7, and has a metal filler 13 disposed therein. The metal filler 13 may be a metal sheet, a metal strip, a metal frame, etc., as long as it is ensured that the metal filler 13 may electrically contact the first conductive layer 10 and the human body. Illustratively, the metal filler 13 may form a partial metal coating on the tip of the lancet 701 and on the surface of the operating mechanism 7, thereby achieving an electrically conductive function.

In this embodiment, the first conductive layer 10 contacts the human body through the metal filler 13 in the lancet 701, so that the static electricity generated by the use of the powder inhalation device is conducted out of the human body, avoiding the effect of electrostatic charge on powder adsorption. In addition, the metal filler 13 can strengthen the structure of the lancet 701, improving the uniformity of its force, and making the lancet 701 more stable when piercing.

The present application also discloses a medicament box including the above powder inhalation device.

An air resistance test experiment of the device can be carried out by means of an air resistance tester (model TPK 2000-R).

In some examples, operation steps of using a commercially available air resistance tester model TPK 2000-R include:

Checking whether a vacuum pump is effectively connected and whether an air tube is connected to an airflow rate controller;

Checking whether the airflow rate controller is effectively connected to a flow rate tester, and whether a power cord and a signal control line are properly connected;

Finding a suitable test adapter, effectively connecting same to an air inlet, and effectively connect a sample to the adapter to check whether air tightness is intact, and optionally, if the presence of a gap between the sample and the adapter results in poor air tightness, a reinforcing device (such as a rubber band or the like) may be used for fastening;

Turning on power to the vacuum pump, the airflow rate tester, and the airflow rate controller;

Viewing a display page of the airflow rate controller;

Clicking a button on the airflow rate controller to test, where test steps include: 1) adjusting an air pressure to 0.5% of a set value (4±0.02 Kpa or ±0.02 Kpa), and waiting for the air pressure to stabilize; 2) removing the sample and the adapter; 3) assembling and tightening joints of the airflow rate tester and the airflow rate controller; 4) testing and reading a flow rate.

The air resistance in the device can be measured by the above operation steps and the air resistance tester, and the flow rate of air in the device is recorded. For example, table 1 below shows standard values for flow rates at different pressures (2 kp, 4 kp); and table 2 below shows flow rate values measured by the air resistance tester (model TPK 2000-R) at different pressures (2 kp, 4 kp).

TABLE 1

Standard values for flow rates at different pressures (2 kp, 4 kp)

| P1 Pressure (kp) | 2 kp | 4 kp |
|---|---|---|
| Flow rate (L/min) | 35.0 ± 3.5 | 48 ± 4.8 |

TABLE 2

Flow rate values measured by air resistance tester (model TPK 2000-R) at different pressures (2 kp, 4 kp)

| P1 pressure | 2 kp | 4 kp |
|---|---|---|
| Number 1 | 36.4 | 49.6 |
| Number 2 | 35.1 | 48.8 |
| Number 3 | 35.3 | 49.3 |
| Number 4 | 35.8 | 49.7 |
| Number 5 | 35.1 | 48.3 |
| Mean (L/min) | 35.54 | 49.14 |

As can be seen from tables 1 and 2, the flow rate values obtained from the device tests according to the present disclosure meet the standard values and the test conclusions are passed.

Although embodiments of the present invention have been shown and described above, it is to be understood that the embodiments described above are exemplary and cannot be construed as limiting the present invention, variations, modifications, substitutions and variations of the above-described embodiments may be made by those of ordinary skill in the art within the scope of the present invention without departing from the principles and purposes of the present invention, and all such changes shall fall within the scope of protection of the claims of the present invention.

List of reference numerals: 1. Carrier plate; 101. Through hole; 102. Annular groove; 103. Air intake slot; 1031. Horizontal slot section; 1032. Oblique slot section; 1033. Draft slot section; 104. First snap-fit groove; 105. Flange; 106. Second snap-fit; 107. Air intake gap; 108. Interference surface; 2. Mouthpiece; 201. Support rib; 202. Recessed area; 3. Capsule chamber; 301. Guiding plate; 3011. Guiding hole; 302. Rib; 4. Sieve mesh; 5. Sieve holder; 501. First snap-fit; 502. Fixing portion; 503. Guide slot; 6. Lower shell; 601. Outer shell; 6011. Opening; 6012. Notch structure; 6013. Limit block; 602. Inner shell; 6021. Side panel; 6022. Auxiliary column; 603. Viewing window; 604. Step; 605. Second snap-fit groove; 7. Operating mechanism; 701. Lancet; 7011. Main oblique piercing surface; 7012. Lateral piercing surface; 702. Guide plate; 703. Backstop; 704. Boat-shaped recess; 705. Cross-shaped protrusion; 8. Upper shell; 801. Closure; 8011. Guide portion; 8012. Interference portion; 9. Hinge pin; 10. First conductive layer; 11. Second conductive layer; 12. Third conductive layer; 13. Metal filler; 14. Pressing rib; 15. Spring.

What is claimed is:

1. A powder inhalation device comprising:

a carrier plate, a through hole being formed in the carrier plate, and an annular groove being provided at an outer periphery of the through hole;

a mouthpiece, the mouthpiece being disposed above the carrier plate and communicating with the through hole; and a capsule chamber, the capsule chamber being disposed under the carrier plate and communicating with the through hole, the capsule chamber also communicating with an outside atmosphere for inhalation of a first airflow;

wherein the powder inhalation device further comprises:

at least one air intake slot, the air intake slot being provided at the outer periphery of the through hole, and the air intake slot comprising a horizontal slot section and an oblique slot section;

wherein the horizontal slot section is located on an upper surface of the carrier plate, the oblique slot section is located on a sidewall of the annular groove, and the horizontal slot section is connected to the oblique slot section, so that a second airflow drawn from the air intake slot creates a turbulent flow at the annular groove;

wherein the air intake slot further comprises a draft slot section;

wherein the draft slot section is located on the upper surface of the carrier plate and is disposed at an end of the horizontal slot section away from the oblique slot section, and the draft slot section and the horizontal slot section and the oblique slot section are integrally formed.

2. The powder inhalation device according to claim 1, wherein the sum of surface areas of the horizontal slot section and the oblique slot section is positively related to an air intake amount of the air intake slot;

an included angle between the horizontal slot section and the oblique slot section is negatively related to the air intake amount of the air intake slot; and/or three air intake slots are provided, the air intake slots being distributed circumferentially uniformly at the outer periphery of the through hole.

3. The powder inhalation device according to claim 1, wherein a sieve mesh is arranged between the mouthpiece and the carrier plate, the sieve mesh is located at the through hole, and the sieve mesh is configured to intercept large particles of powder that have not been broken up.

4. The powder inhalation device according to claim 1, wherein a sieve holder is provided inside the mouthpiece;

the sieve holder is partially provided in the annular groove and forms an airflow channel with the air intake slot, and at least two first snap-fits are provided at an outer periphery of the sieve holder;

the carrier plate is provided with at least two first snap-fit grooves, the first snap-fit grooves corresponding to and matching the first snap-fits; and the sieve holder is snap-fitted and fixed to the carrier plate by the first snap-fits and the first snap-fit groove, and a sieve mesh is provided in the sieve holder.

5. The powder inhalation device according to claim 4, wherein a fixing portion is provided at the bottom of the sieve holder; and the sieve mesh is provided at the fixing portion, and the sieve mesh and the fixing portion are fixedly connected by means of hot melting.

6. The powder inhalation device according to claim 1, further comprising a lower shell, the top of which is open;

wherein the carrier plate is hinged with the lower shell and is snap-fitted to the top of the lower shell; and the capsule chamber is housed inside the lower shell.

7. The powder inhalation device according to claim 6, wherein the lower shell comprises an outer shell and an inner shell;

the outer shell is provided with an opening on each side of the capsule chamber, and two sides of the opening are symmetrically provided with notch structures;

the inner shell has upwardly extending side panels on both sides, the side panels are at least partially engaged with the notch structures to secure the inner shell within the outer shell, while part of the side panel is of a transparent structure and a viewing window is formed at the corresponding opening;

steps are provided on two sides of the top of the lower shell, and each of the steps is provided with a second snap-fit groove at a hinge point away from the lower shell;

flanges are provided on both sides of the carrier plate, and each of the flanges is provided with a second snap-fit at a hinge point away from the carrier plate; and the flange is provided on the step and is snap-fitted and fixed to the second snap-fit groove by the second snap-fit, so that the carrier plate is detachably connected to the lower shell.

8. The powder inhalation device according to claim 7, wherein the notch structure is provided with a limit block, and the limit block is configured to limit the position of the inner shell; and an auxiliary column is provided at an inner bottom of the inner shell, and the auxiliary column is configured to correct and position the capsule chamber.

9. The powder inhalation device according to claim 7, wherein an inner wall of the mouthpiece and an inner wall of the capsule chamber are provided with a first conductive layer;

an outer surface of the lower shell is provided with a second conductive layer; and the first conductive layer is electrically connected to the second conductive layer so that static electricity generated by the use of the powder inhalation device is conducted out through a human body.

10. The powder inhalation device according to claim 6, wherein an air intake gap is formed between the carrier plate and the lower shell, and the air intake gap is in communication with the bottom of the capsule chamber, so that the first airflow enters the capsule chamber through the air intake gap.

11. The powder inhalation device according to claim 6, further comprising an operating mechanism with a lancet;

wherein the operating mechanism is movably arranged on a sidewall of the lower shell, and the operating mechanism is configured as a dual function actuator;

in a first actuation, the operating mechanism is capable of driving an upper shell to open; and in a second actuation, the operating mechanism is capable of driving the lancet to pierce a target capsule in the capsule chamber.

12. The powder inhalation device according to claim 11, wherein the operating mechanism has guide plates parallel to the lancet, and a backstop is provided at an end of each of the guide plates close to the capsule chamber;

a guiding plate is provided on a side of the capsule chamber facing the operating mechanism, and the guiding plate is formed with a guiding hole; and the guide plate is slidably inserted into the guiding hole, and an anti-release function is realized by the backstop.

13. The powder inhalation device according to claim 11, further comprising the upper shell, the bottom of which is open;

wherein one side of the upper shell is hinged with the carrier plate, and the other side of the upper shell is provided with a closure;

an interference surface is provided on a side of the carrier plate close to the operating mechanism;

a boat-shaped recess is provided at the top of the operating mechanism;

when the upper shell is in a closed state, the closure is located just inside the boat-shaped recess and is held against the interference surface; and only when an acting force exerted by the boat-shaped recess on the closure is larger than an interference force between the closure and the interference surface, the closure is capable of being disengaged from the interference surface and automatically opening the upper shell.

14. The powder inhalation device according to claim 13, wherein the closure comprises a guide portion and an interference portion arranged in sequence from bottom to top; and the guide portion is in sliding fit with the boat-shaped recess to provide an acting force for driving the interference portion away from the interference surface.

15. The powder inhalation device according to claim 11, wherein an inner wall of the mouthpiece and an inner wall of the capsule chamber are provided with a first conductive layer;

the lancet is a conductive lancet;

a third conductive layer is provided on a surface of the operating mechanism, or the inside of the operating mechanism is provided with a third conductive layer extending to the outside; and the first conductive layer is electrically connected to the third conductive layer by the lancet so that static electricity generated by the use of the powder inhalation device is conducted out through a human body.

16. The powder inhalation device according to claim 11, wherein an end of the lancet close to the capsule chamber is of a multifaceted structure, the multifaceted structure comprising a main oblique piercing surface and lateral piercing surfaces on two sides of the main oblique piercing surface.

17. The powder inhalation device according to claim 11, wherein a spring is arranged between the capsule chamber and the operating mechanism;

a rib is provided on a side of the capsule chamber facing the operating mechanism;

a cross-shaped protrusion is provided on a side of the operating mechanism facing the capsule chamber, and four sides of the cross-shaped protrusion extend outward and form a reinforcing rib structure in the operating mechanism; and two ends of the spring are fitted over the rib and the cross-shaped protrusion, respectively.

18. A medicament box, comprising a powder inhalation device according to claim 1.

19. A powder inhalation device comprising:

a carrier plate, a through hole being formed in the carrier plate, and an annular groove being provided at an outer periphery of the through hole;

a mouthpiece, the mouthpiece being disposed above the carrier plate and communicating with the through hole; and a capsule chamber, the capsule chamber being disposed under the carrier plate and communicating with the through hole, the capsule chamber also communicating with an outside atmosphere for inhalation of a first airflow;

wherein the powder inhalation device further comprises:

at least one air intake slot, the air intake slot being provided at the outer periphery of the through hole, and the air intake slot comprising a horizontal slot section and an oblique slot section;

wherein the horizontal slot section is located on an upper surface of the carrier plate, the oblique slot section is located on a sidewall of the annular groove, and the horizontal slot section is connected to the oblique slot section, so that a second airflow drawn from the air intake slot creates a turbulent flow at the annular groove, wherein the powder inhalation device further comprises a lower shell, the top of which is open;

wherein the carrier plate is hinged with the lower shell and is snap-fitted to the top of the lower shell; and the capsule chamber is housed inside the lower shell, wherein the powder inhalation device further comprises an operating mechanism with a lancet;

wherein the operating mechanism is movably arranged on a sidewall of the lower shell, and the operating mechanism is configured as a dual function actuator;

in a first actuation, the operating mechanism is capable of driving the upper shell to open; and in a second actuation, the operating mechanism is capable of driving the lancet to pierce a target capsule in the capsule chamber, wherein an inner wall of the mouthpiece and an inner wall of the capsule chamber are provided with a first conductive layer;

the lancet is a non-conductive lancet, and the lancet extends to a surface of the operating mechanism and has a metal filler disposed therein; and the first conductive layer contacts a human body through the metal filler so that static electricity generated by the use of the powder inhalation device is conducted out through the human body.

* * * * *